United States Patent [19]
Hart

[11] Patent Number: 5,884,625
[45] Date of Patent: *Mar. 23, 1999

[54] ORAL APPLIANCE FOR DELIVERING GAS TO THE RETROGLOSSAL AREA

[76] Inventor: William T. Hart, 981 Cabernet Ct., Murphys, Calif. 95247

[*] Notice: This patent issued on a continued prosecution application filed under 37 CFR 1.53(d), and is subject to the twenty year patent term provisions of 35 U.S.C. 154(a)(2).

[21] Appl. No.: 677,491

[22] Filed: Jul. 9, 1996

[51] Int. Cl.⁶ ............. A61M 16/00; A62B 9/06; A62B 7/00; F16K 31/02
[52] U.S. Cl. ............. 128/207.14; 128/207.15; 128/204.18; 128/204.23
[58] Field of Search ............. 128/200.26, 207.14, 128/201.26, 204.11, 204.18, 207.15, 206.29, 205.24, 204.23; 137/597

[56] References Cited

U.S. PATENT DOCUMENTS

| | | | |
|---|---|---|---|
| 900,343 | 10/1908 | Barnes | 128/207.14 |
| 1,266,856 | 5/1918 | Ramsay | 128/207.14 |
| 2,459,273 | 1/1949 | Freedland . | |
| 2,669,988 | 2/1954 | Carpenter . | |
| 3,126,002 | 3/1964 | Owens . | |
| 3,730,179 | 5/1973 | Williams . | |
| 3,905,362 | 9/1975 | Eyrick et al. . | |
| 4,112,936 | 9/1978 | Blachly . | |
| 4,169,473 | 10/1979 | Samelson . | |
| 4,170,230 | 10/1979 | Nelson . | |
| 4,198,967 | 4/1980 | Dror . | |
| 4,260,378 | 4/1981 | O'Neil . | |
| 4,270,531 | 6/1981 | Blachly et al. . | |
| 4,304,227 | 12/1981 | Samelson . | |
| 4,425,911 | 1/1984 | Luomanen et al. | 128/200.26 |
| 4,495,945 | 1/1985 | Liegner | 128/200.26 |
| 4,513,741 | 4/1985 | Demi | 128/205.25 |
| 4,676,240 | 6/1987 | Gardy . | |
| 4,856,991 | 8/1989 | Breads et al. . | |
| 4,936,298 | 6/1990 | Nishina et al. | 128/205.13 |
| 4,938,212 | 7/1990 | Snook et al. | 128/205.24 |
| 5,117,816 | 6/1992 | Shapiro et al. . | |
| 5,146,913 | 9/1992 | Khorsandiam et al. | 128/200.26 |
| 5,181,505 | 1/1993 | Lew et al. | 128/200.26 |
| 5,195,513 | 3/1993 | Sinko et al. | 128/207.14 |
| 5,203,324 | 4/1993 | Kinkade | 128/207.14 |
| 5,443,060 | 8/1995 | Visveshwana et al. | 128/207.14 |
| 5,507,282 | 4/1996 | Younes . | |
| 5,522,382 | 6/1996 | Sullivan et al. | 128/204.21 |
| 5,626,128 | 5/1997 | Bradley et al. | 128/207.14 |

FOREIGN PATENT DOCUMENTS

| | | | |
|---|---|---|---|
| 0402951 | 12/1990 | European Pat. Off. | 128/204.26 |
| 35 43 931 A 1 | 6/1987 | Germany . | |
| 44 45 652 A 1 | 6/1996 | Germany . | |
| PCT/SE89/00500 | 4/1990 | WIPO . | |
| PCT/SE90/00464 | 1/1991 | WIPO . | |

OTHER PUBLICATIONS

John R. Bach, M.D. et al., "Mouth Intermittent Positive Pressure Ventilation in the Management of Postpolio Respiratory Insufficiency", Chest/91/6/Jun. 1987, pp. 859–864.

(List continued on next page.)

Primary Examiner—Kimberly L. Asher
Attorney, Agent, or Firm—Anderson & Adamson; C. Douglas DeFreytas

[57] ABSTRACT

An appliance is provided for installation within the mouth of an individual to prevent obstruction of the natural airway of the individual and to enhance natural ventilation during sleep. The appliance is hollow and is custom-molded to the oral cavity for biasing tissues surrounding the user's natural airway to keep the airway open. An external positive air supply is also provided which connects to a tube extending from the appliance and forces air through the hollow appliance to a rear opening of the appliance in the user's retroglossal area. A sensor provides control information to the positive air supply by sensing relative pressure in the user's oral cavity. The natural breathing cycle is thus enhanced but not controlled by the appliance.

7 Claims, 2 Drawing Sheets

OTHER PUBLICATIONS

John R. Bach, M.D. and Augusta S.Alba, M.D., "Sleep and Nocturnal Mouthpiece IPPV Efficiency in Postpoliomyelitis Ventilator User's ", *Chest*/106/6/Dec. 1994, pp. 1705–1710.

John R. Bach, M.D., "Mask' Ventilation Doesn't Have to Be through the Nose", *Chest*/101/4/Apr. 1992, pp. 1182–1183.

John R. Bach, M.D., "Mechanical Exsufflation, Nonivasive Ventilation, and New Strategies for Pulmonary Rehabilitation and Sleep Disorder Breathing", *Bull. N.Y. Acad. Med.*, vol. 68, No. 2, Mar.–Apr. 1992, pp. 321–340.

Promotional Pamphlet "The Klearway Oral Appliance", Great Lakes Orhtodonitics, Ltd., 1995, 12 pamphlet pages.

Promotional Sheet "The Snore Appliance", Dyna Flex, Ltd., St. Louis, MO—1 page.

Article "Snoring, A Reason to be Concerned", Great Lakes Orthodonitcs, Ltd.—2 pages.

Promotional Pamphlet "Nocturnal Airway Patency Appliance", Great Lakes Orthodontics, Ltd., 12 pamphlet pages.

Article "Snoring" The University Language and The Virginia Partial, Johns Dental Laboratories, Oral Support, Winter 95/96–2 pages.

D.L. Grim, Newsletter, Medical Resource Center, Olympia WA, 3 pages.

Promotional Sheet "Silencer", Johns Dental Laboratories, Terre Haute, IN—1 page.

W. Schmidt–Nowara, A. Lowe, L. Weigand, R. Cartwright, F. Perez–Guerra and S. Menn—"Oral Apppliances for the Treatment of Snoring and Obstructive Sleep Apnea: A Review"–An American Sleep Disorders Association Review—*Sleep* 18(6):501–510—1995 American Sleep Disorder Association and Sleep Research Society, pp. 501–509.

Standards of Practice Committee of the American Sleep Disorders Association and Sleep Research Society—"Practice Parameters for the Treatment of Snoring and Obstructive Sleep Apnea with Oral Appliances"–*Sleep* 18(6):511–513—1195 American Sleep Disorders Association and Sleep Research Society, pp. 511–513.

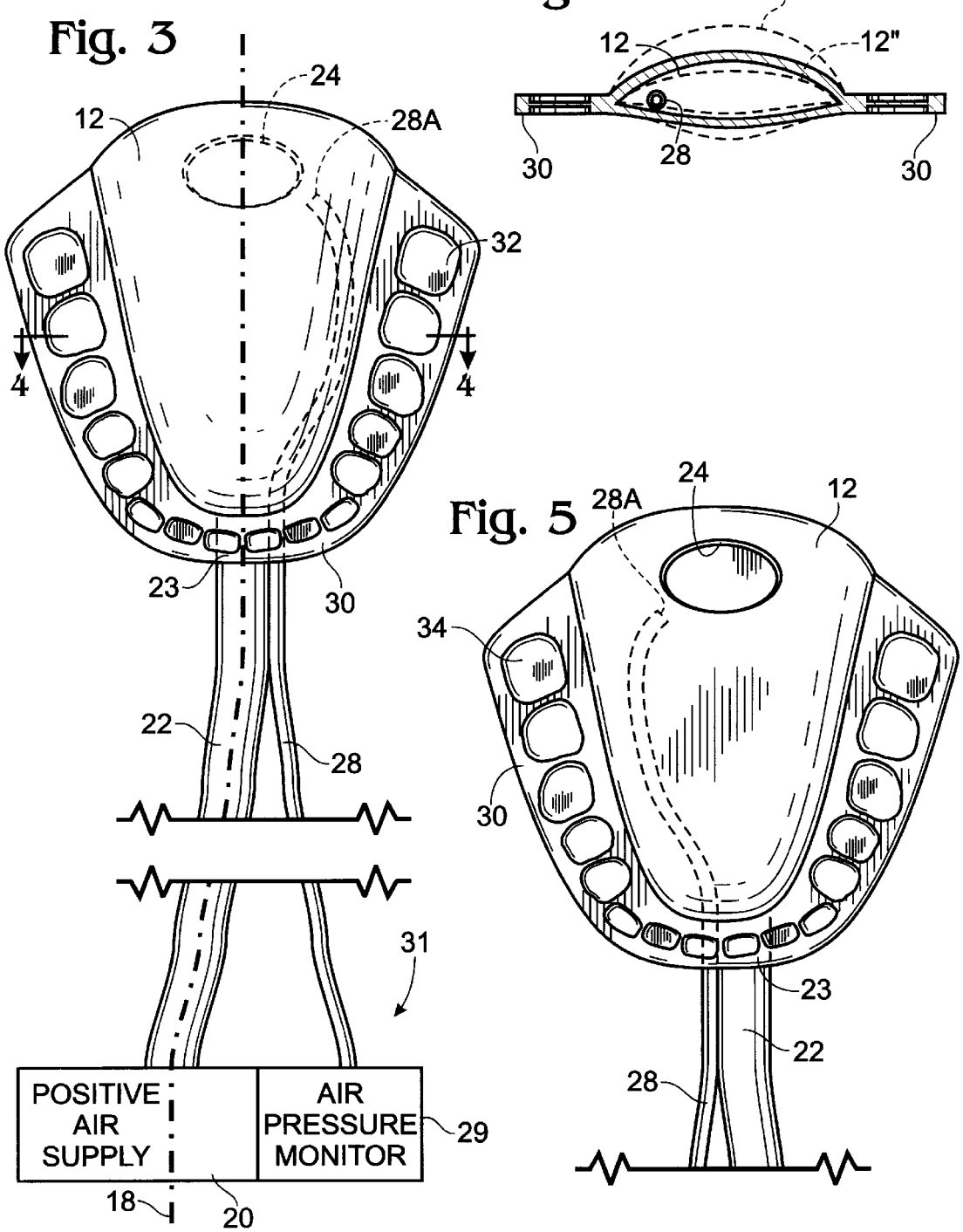

ORAL APPLIANCE FOR DELIVERING GAS TO THE RETROGLOSSAL AREA

BACKGROUND OF THE INVENTION

1. Field of the Invention

This invention relates to appliances for preventing airway occlusion during sleep in individuals who suffer from sleep apnea or snoring, or both. More particularly it relates to an appliance that is inserted into a user's oral cavity for providing an air pathway through the oral cavity.

Airway occlusion during sleep may cause cessation of breathing (apnea) and lead to undesirable physiologic changes of hypoxemia and hypercapnia. Persons suffering from sleep apnea are at risk for systemic and pulmonary hypertension, arrhythmias leading to sudden cardiac death, and accidents due to hypersomnolence.

Airway occlusion may be caused by decline in upper airway dilator muscle tone, especially the genioglossus muscle. Redundant pharyngeal tissue and edema may be contributing factors. Sleeping on the back may exacerbate airway occlusion due to the added effect of gravity on the tongue. Sleep apnea is most pronounced during the inspiratory phase of breathing (inhalation). In patients suffering from sleep apnea or snoring, or both, the retroglossal area is usually the most obstructed part of the airway.

2. Related Art

Various devices have been developed to facilitate breathing for those suffering from airway occlusion. One such device, as disclosed in U.S. Pat. No. 4,676,240, issued to Gardy on Jun. 30, 1987, provides a mechanism which holds the tongue forward in a vacuum chamber. Another device is disclosed in U.S. Pat. No. 4,170,230, issued to Nelson on Oct. 9, 1979, which allows the user to breathe through his or her mouth without drying out the mouth. Another device, as disclosed in U.S. Pat. No. 4,198,967, issued to Dror on Apr. 22, 1980, teaches a method of holding the tongue in an unconscious or semi-conscious individual as an adjunct to resuscitation of the individual.

U.S. Pat. No. 3,370,179, issued to Williams on May 1, 1973, discloses a combination resuscitating, aspirating and gastric draining apparatus which includes a tube extended down the throat of a victim in combination with a draining apparatus. This apparatus uses a conventional resuscitating supply source acting through a demand valve and an elongate tube extending down the throat Appliances are also known which provide for nasal delivery of a positive air supply during both inspiration and exhalation. None of these inventions compensate for redundant pharyngeal tissue and laxity of airway dilator muscle tone or provide a positive air supply via an oral appliance.

SUMMARY OF THE INVENTION

The present invention overcomes these deficiencies of the existing art. One aspect of the invention prevents airway occlusion during sleep, minimizing sleep apnea and snoring, by maintaining adequate opening in a user's retroglossal area. Another aspect of the invention provides controlled positive air pressure directly into the same area to facilitate natural breathing. Once a diagnosis of snoring or sleep apnea is made, a simple, comfortable appliance, operable by a patient without direct medical assistance can be custom made according to the invention to treat those conditions, for reducing the deleterious physiologic effects snoring and sleep apnea produce.

In a preferred method for manufacturing a sleep-apnea-and-snoring-reducing appliance according to the invention, a user's dental impression is used in making the appliance for wearing by that user during sleep.

In a first embodiment of the present invention, a hollow, body is molded to the user's oral cavity and includes an integral, generally C-shaped lip-like member conforming to the user's bite impression. The appliance is thus natural and comfortable when inserted in the user's oral cavity. Furthermore, the molded design naturally secures the appliance in the desired position during use with no effort by the user, which is a necessary feature inasmuch as the appliance is intended to be worn while the user is asleep. A tube extends through the user's teeth and lips. An opening is formed at the rear of the body directed downward into the user's airway. The typical and undesirable characteristic of a patient suffering from sleep apnea or snoring is the tendency of the tissues in the retroglossal area, typically the posterior portion of the tongue and the soft palate, to block the airway, interfering with normal breathing. This feature of the present invention effectively prevents such blockage by splinting the tissues in the retroglossal area, maintaining an open airway.

In addition, an embodiment of this invention utilizes an external positive air supply which is coupled to the tube extending from the body. When positive air pressure is fed into the appliance, the body of the appliance, being constructed of a durable material such as acrylic, easily maintains positive pressure that forces air directly into the user's retroglossal area while the patient sleeps in various positions. Certain persons may also benefit by splinting during exhalation to avoid airway collapse as they exhale.

The floor of the appliance rests above the tongue. This floor is shaped from a mold of the person's own palate. This personal shape facilitates a natural swallowing pattern, lessening saliva and preventing a gag reflex response.

These and other advantages and features of the present invention will be apparent from the preferred embodiment described in the following detailed description and in the accompanying drawings.

BRIEF DESCRIPTION OF THE DRAWINGS

FIG. 3 is a plan view of the appliance of FIG. 1 showing connection to an air pressure source.

FIG. 4 is a cross-sectional view of the appliance taken generally along the line 4—4 of FIG. 3 showing the body bot in expanded and non-expanded mode.

FIG. 5 is a bottom view of the appliance of FIG. 1 showing the opening which is situated in a user's retroglossal area in normal use.

DETAILED DESCRIPTION OF THE PREFERRED EMBODIMENT

Figure 1:
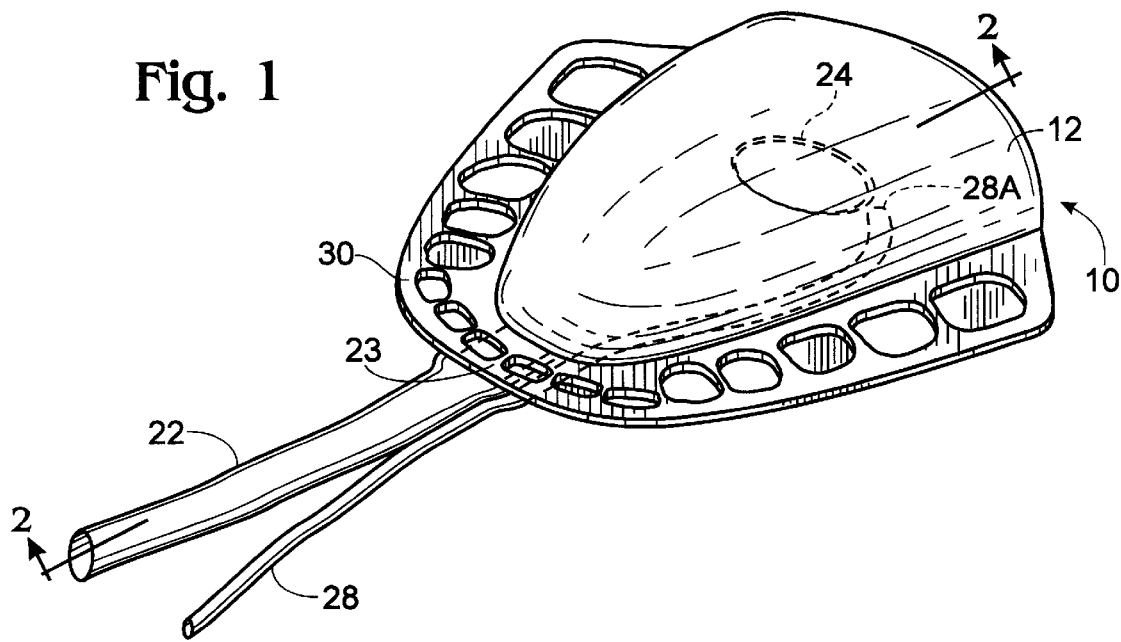
FIG. 1 is a perspective view of an appliance made according to the invention.
Figure 2:
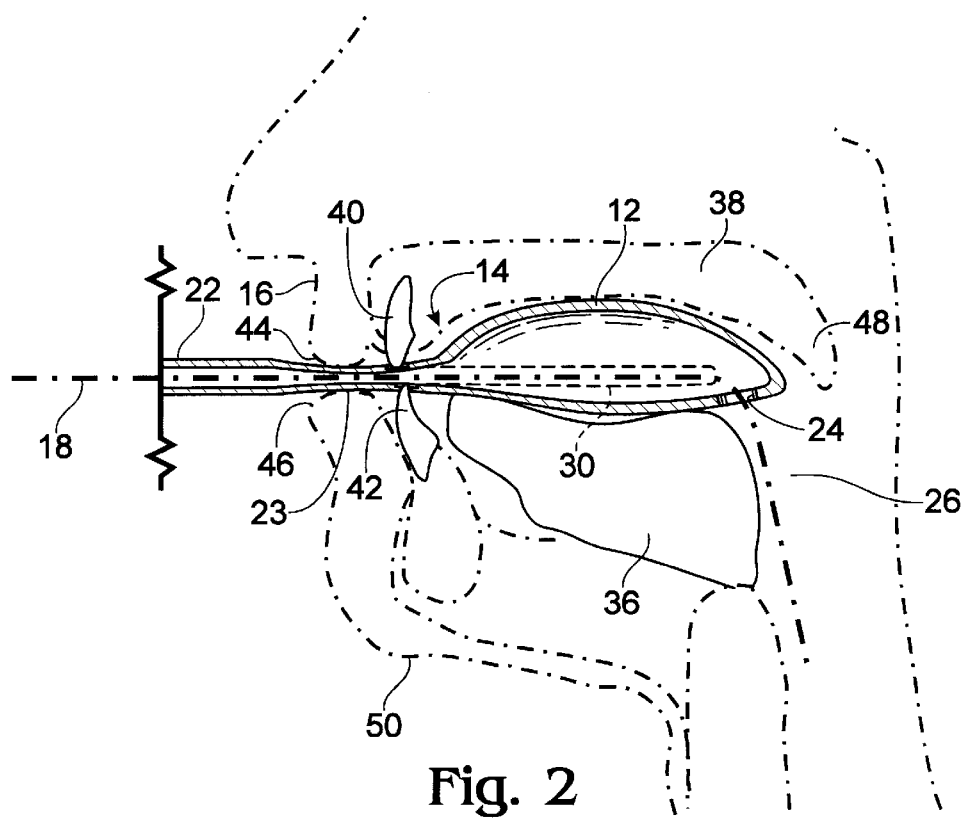
FIG. 2 is a cross-sectional view taken generally along the line 2—2 of FIG. 1 illustrating the appliance of FIG. 1 inserted into a user's oral cavity.

Referring to the drawings, an oral appliance constructed in accordance with the present invention is shown generally at 10 in FIG. 1. FIG. 2 depicts a cross-sectional view of the appliance taken along line 2—2 in FIG. 1, illustrating a hollow body 12 of the appliance installed in the oral cavity 14 of a user 16. In FIG. 3 a top view of the appliance is shown illustrating an air pathway 18 from an external positive air supply 20, through a tube 22, into a first opening 23 in the body, through hollow body 12, to a second opening 24, which, in the operative position, opens downwardly in the user's retroglossal area 26 as seen in FIG. 2. Body 12 thus forms what is also referred to as an enlarged chamber extending between the first and second openings. As can be seen, one end of tube 22 is attached to body 12 to provide fluid communication through opening 23 between the enlarged chamber in body 12 and the exterior of the user's oral cavity. Accordingly, tube 22 and body 12 comprise what is also referred to as means defining an air supply pathway. Referring again to FIG. 3, a second tube 28 is shown communicating from a point adjacent to opening 24, following generally alongside tube 22, and connected to the external positive air supply 20. Air supply 20 is a conventional air supply, such as one having the proprietary name "BIPAP S/T-D" sold by Respironics, Inc. Tube 28 is connected to a conventional air pressure monitor 29 such as model no. 302220 also sold by Respironics, Inc. Tube 28 and monitor 29 form what is generally referred to as a sensor 31. Conventional air supplies are also available that have the sensor built into them, thereby avoiding the need for a separate sensor 31.

A lip 30 as seen in FIGS. 1, 3, 4, and 5 extends out from the anterior outer edges of body 12. Lip 30 is integrally attached to body 12 and includes indentations, such as shown at 32, 34. These indentations are preferably formed as dental impressions using conventional techniques. Lip 30 and body 12 are preferably made of acrylic using conventional methods. When installed in a user's oral cavity, as shown in FIG. 2, the appliance lodges vertically between the user's tongue 36 and the user's hard palate 38. Passing between user's teeth, such as upper tooth 40 and lower tooth 42, and between the user's lips including upper lip 44 and lower lip 46, tube 22 is seen to communicate outside the user's oral cavity 14.

Appliance 10 is naturally held in proper operative position by the shape of body 12 conforming nestingly to the user's oral cavity 14, bounded by soft palate 48, tongue 36, and hard palate 38. Accordingly, a user's tooth, corresponding to and naturally nesting in an associated indentation 32, assists in holding appliance 10 in the desired position in the user's oral cavity 14. Another user's tooth, corresponding to and naturally nesting in indentation 34, further assists in securing the appliance. Similarly, all of the user's teeth will have corresponding indentations in lip 30, such that appliance 10 is securely held immobile with reference to the user's oral cavity 14 when installed by user 16.

Appliance 10 may be used passively, without an external positive air supply, as shown in FIGS. 1 and 2. In this embodiment, no sensor tube is necessary and the appliance performs its function by splinting the tissues such as the soft palate 48 preventing constriction as against the rear of tongue 36 and providing an uninterrupted air pathway 18 between ambient air and the user's retroglossal area.

In the embodiment particularly shown in FIG. 3, appliance 10 is installed in a user's oral cavity 14 and connected to an external positive air supply 20 with tube 22 and sensor 31 using a second tube 28, which terminates at end 28A near opening 24. In operation, air is forced into hollow body 12, via tube 22 from air supply 20, when triggered by monitor 29. Monitor 29 is designed to sense the reduced pressure in tube 28 when the user begins to inhale.

Body 12 may also be composed of a resilient material, such as a form of silicone, which expands slightly when positive air pressure is applied, as shown in FIG. 4 by expanded body 12'. Air is then inspired by the user through opening 24 collapsing body 12 slightly to a deflated position as shown at 12". The air supply is turned off when increased air pressure is sensed when the user is no longer inhaling. The user may exhale around the appliance, or through it in the case where no air supply is attached.

In the preferred embodiment of the present invention, appliance 10 is tailored to an individual by impressions of the user's oral cavity and teeth using conventional methods. It will be understood by those familiar with the art that "tooth impressions" in the present context includes impressions of a user's bony oral cavity structure where the user lacked full dentition, or lacked teeth altogether.

To manufacture an appliance in accordance with the present invention, a moldable hollow elongate body 12 the approximate size of a user's oral cavity is formed. Then, a moldable horseshoe-shaped lip 30 is formed which protrudes in a place concentrically from the body 12. The body 12 with lip 30 is then inserted into the user's oral cavity, while the material is still moldable, the user clenches his or her teeth on lip 30 and the appliance 10 is molded in conformance with the user's oral cavity structure. First and second openings 23 and 24 are then formed on the molded appliance. A tube 22 is then attached to first opening 23. A second tube 28, if required, is then attached through first opening 23 and through hollow body 12 to a point adjacent to second opening 24.

During the impression-taking phase of manufacture of the appliance, the user's lower jaw is preferably held slightly forwardly from a relaxed-jaw position. When the finished appliance is installed by the same user, the nesting effect described herein urges the user's lower jaw 50 to a slightly forward position from a relaxed-jaw state. This feature further enhances the operation of the appliance by holding the user's tongue 36 forward and away from the user's soft palate 48, minimizing constriction caused by the juxtaposition of the tongue 36 and the soft palate 48.

It will thus be appreciated that appliance 10 provides improved treatment of occlusive sleep apnea. A defined, unrestricted airway is provided to the posterior of a user's oral cavity, and more particularly to a downwardly directed opening in the retroglossal area. An optional positive air supply thus directs a positive flow of air into the throat, beyond obstructing tissue. The appliance conforms to the user's oral cavity and teeth, making it comfortable to use. The addition of the positive air supply to the dental appliance formed by lip 30 in itself provides assistance to the patient's breathing.

Variations in form and detail of the preferred embodiment may be made without departing from the scope of the described invention as literally set forth in the claims and as provided under the doctrine of equivalents. For example the appliance could be constructed of rigid material yet still provide the requisite ventilation assistance of the invention. The appliance body could be made smaller and other means could be used to anchor the body in the oral cavity.

I claim:

1. An oral appliance for facilitating breathing comprising:
    a hollow elongate body adapted for complete insertion into a user's oral cavity, the body defining an air pathway and composed of a molded resilient material, the body spatially conforming to the user's oral cavity and including a first opening positioned anteriorly during use and a second opening posteriorly during use in the user's retroglossal area;
    a lip extending from the body sagittally and anteriorly during use for grasping between the user's teeth, the lip formed from upper and lower dental impressions of the user's teeth for holding the user's teeth slightly apart and the user's lower jaw slightly forward from a relaxed-jaw position when placed in the user's oral cavity with the teeth positioned in the dental impressions, the lip being molded to form the first opening;

a tubular member coupled at one end to the lip for communication with the first opening, the other end extending distally of the lip; and an air pressure source coupled to the other end of the tubular member for applying positive air pressure through the body to the second opening.

2. An oral appliance for facilitating breathing comprising:

means defining an air supply pathway having an opening positioned posteriorly during use in the user's retroglossal area;

means for securing the means defining an air supply pathway with the opening positioned in the user's retroglossal area, the means for securing the means defining an air supply pathway comprising a lip attached to the means defining an air supply pathway and extending along a length of the means defining an air supply pathway for grasping between the user's teeth; and an external positive air pressure source coupled to the means defining an air supply pathway for applying positive air pressure to the opening, and thereby applying positive air pressure to the retroglossal area.

3. The oral appliance of claim 2 in which the lip is adapted for spatially conforming to the user's bite when the user's lower jaw is positioned slightly anteriorly from a relaxed-jaw position in relation to the upper jaw.

4. The oral appliance of claim 2 in which the lip is adapted for spatially conforming to the user's bite.

5. An oral appliance for facilitating breathing comprising:

a hollow elongate body adapted to fill a user's oral cavity, the body having a first opening in one end, a second opening in the other end, and an enlarged chamber extending between the first and second openings, the second opening facing transversely to a straight line extending between the first and second openings;

means for securing the body in the user's oral cavity with the first opening positioned adjacent to the front of a user's oral cavity and the second opening facing downwardly in the user's retroglossal area the means for securing the body comprising a lip attached to the body and extending along a length of the body for grasping between the user's teeth;

a tubular member extending from the body for providing fluid communication, through the first opening into the chamber, between the interior of the second opening and the exterior of the user's oral cavity; and an external positive air pressure source coupled to the tubular member for applying positive air pressure through the body to the second opening, and thereby pressurizing the soft tissues of the retroglossal area, including the tongue and soft palate.

6. The oral appliance of claim 5 in which the lip is adapted for spatially conforming to the user's bite.

7. The oral appliance of claim 5 in which the lip is adapted for spatially conforming to the user's bite when the user's lower jaw is positioned slightly anteriorly from a relaxed-jaw position in relation to the upper jaw.

* * * * *